(12) United States Patent
Meehan

(10) Patent No.: US 8,344,032 B2
(45) Date of Patent: Jan. 1, 2013

(54) COMPOSITION FOR ENHANCING ATHLETIC PERFORMANCE

(76) Inventor: Kevin Meehan, Jackson, WY (US)

( * ) Notice: Subject to any disclaimer, the term of this patent is extended or adjusted under 35 U.S.C. 154(b) by 14 days.

(21) Appl. No.: 12/896,162

(22) Filed: Oct. 1, 2010

(65) Prior Publication Data

US 2011/0236535 A1    Sep. 29, 2011

Related U.S. Application Data

(60) Provisional application No. 61/318,081, filed on Mar. 26, 2010, provisional application No. 61/357,045, filed on Jun. 21, 2010.

(51) Int. Cl.
*A61K 31/121* (2006.01)
*A61K 9/20* (2006.01)
*A61K 9/48* (2006.01)

(52) U.S. Cl. ......... 514/675; 424/400; 424/451; 424/464

(58) Field of Classification Search ................ None
See application file for complete search history.

(56) References Cited

U.S. PATENT DOCUMENTS

| 5,714,515 | A * | 2/1998 | Bunger ......................... 514/557 |
|---|---|---|---|
| 6,277,842 | B1 | 8/2001 | Carthron |
| 2001/0051134 | A1 | 12/2001 | Pandya |
| 2002/0173546 | A1 | 11/2002 | Rath |
| 2004/0043013 | A1 | 3/2004 | McLeary |
| 2004/0067224 | A1 | 4/2004 | Ernest |
| 2004/0081708 | A1 | 4/2004 | Baxter |
| 2004/0204382 | A1 * | 10/2004 | Henderson et al. ............. 514/52 |
| 2006/0083793 | A1 | 4/2006 | Gardiner et al. |
| 2006/0128643 | A1 | 6/2006 | Kaddurah-Daouk et al. |
| 2008/0038367 | A1 | 2/2008 | Saloum |
| 2010/0074969 | A1 | 3/2010 | Hughes et al. |

OTHER PUBLICATIONS

Marriage et al. Nutritional cofactor treatment in mitochondrial disorders. J Am Diet Assoc. 2003;103:1029-1038.*

* cited by examiner

*Primary Examiner* — Daniel Sullivan
*Assistant Examiner* — Peter Anthopolos
(74) *Attorney, Agent, or Firm* — Marger Johnson & McCollom, P.C.

(57) ABSTRACT

A composition including a plurality of active ingredients. A first active ingredient of the active ingredients is pyruvate. For each other active ingredient, an amount of that active ingredient is proportionally less than an amount of the first active ingredient. The composition can affect ATP and Krebs efficiency when ingested by an animal.

8 Claims, No Drawings

COMPOSITION FOR ENHANCING ATHLETIC PERFORMANCE

CROSS-REFERENCE TO RELATED APPLICATIONS

This application is related to U.S. application Ser. No. 10/386,786, filed Mar. 12, 2003, now abandoned, which is incorporated herein by reference in its entirety. This application claims the benefit of U.S. Provisional Application Ser. No. 61/318,081, filed Mar. 26, 2010, and U.S. Provisional Application Ser. No. 61/357,045, filed Jun. 21, 2010, the contents of each is incorporated herein by reference in its entirety.

TECHNICAL FIELD

This disclosure relates generally to a composition for enhancing athletic performance. More particularly, this disclosure relates to a composition formulated to increase ATP and Krebs efficiency when ingested by an animal (e.g., human).

BACKGROUND

There are a number of liquid compositions or diluted mixtures sold in commerce having names such as "activity drinks," "sports drinks," "energy drinks," "nutrient drinks," and the like. These beverages are advertised to ameliorate physiologic symptoms resulting from the loss of carbohydrates, electrolytes, vitamins, minerals, amino acids, and other important nutrients, during heavy exercise. As those skilled in the art will appreciate, athletic performance, i.e. physical exercise, comprises many different categories of activities, including activities requiring strength, speed, and/or endurance. As those skilled in the art will further appreciate, environmental factors, including temperature, air purity, elevation, humidity, and the like, can markedly affect a person's physical work capacity.

It is thought that muscle activity is primarily based on a very fundamental biochemical mechanism, the breakdown of energy-rich phosphate bonds. Adenosine triphosphate ("ATP") is one source of such phosphate bonds at the cellular level. ATP is the direct source of energy for muscle work and, some believe, comprises the only form of chemical energy which can be converted by muscle tissue into mechanical work.

During high physical activity of the body, the ATP level in the muscles diminishes rapidly. Several substrates are available as sources for replenishing the ATP. When there is low physical activity, metabolism of fats is primarily responsible for ATP production. At higher activity rates, glycogen in the muscle is the major energy supply. The energy from glycogen is released in exercising muscles up to three times as fast as the energy from fat. It is known in the art that exercise of a moderate intensity cannot be maintained without sufficient carbohydrate stores within the body. Carbohydrates are the fuel from which body cells obtain energy for cellular activities and the major portion of carbohydrates utilized by the body are used for ATP production. The energy required for developing athletic activity, and indeed for all muscular work, comes primarily from the oxidation of glycogen stored in the muscles.

Glycogen can be used either relatively slowly via the complete glycolysis and oxidative phosphorylation to form carbon dioxide, water and 38 moles of ATP per mole of glucose. The basic biochemical pathway being: $C_6H_{12}O_6 + 6O_2 \rightarrow 6CO_2 + 6H_2O +$ energy (heat, ATP). This happens not all at once but in many small steps, to control the release of energy. Each step uses one or more enzymes; some use ATP for activation energy. The first process is sometimes called Glycolysis, where, using enzymes, glucose is cleaved into two pieces, and some ATP and NADH are formed. Subsequently, the Krebs cycle transfers electrons, $H^+$ and energy from C—H bonds to $NAD^+$, making NADH. In addition, some ATP is formed. The Krebs cycle occurs in the center of the mitochondrion (inside inner membrane).

Thereafter, an electron transport chain transfers the energy from NADH to produce more than 30 moles of ATP. This happens on the inner membrane of the mitochondrion. Energy is used in small steps to push $H^+$ ions across the membrane. They pile up, then flow through an opening in ATP synthase (an enzyme), where the energy of the flow is used to make ATP.

When exercise is very intensive, i.e. so intensive that the respiratory and cardiovascular systems of the body do not have sufficient time to deliver oxygen to the muscles, the energy for this activity will be delivered almost exclusively from anaerobic metabolism, and much less ATP per molecule of glucose is produced.

Fatigue during high intensity exercise may be viewed as the result of a simple mismatching between the rate at which ATP is utilized and the rate at which ATP is produced in working muscles. The attention, given over the last two decades to the study of the limitations of ATP production, leads to the conclusion that the cause of fatigue may be the inability of the metabolic machinery to provide ATP fast enough for the energy needs of the working muscles to sustain force production.

Furthermore, during relatively extended periods of heavy muscle work, the work capacity of an individual is limited by several factors, such as low blood sugar concentration and loss of liquid by transpiration. In the last decade the use of liquid drinks containing carbohydrates during exercise has become more and more accepted as a stimulus during endurance performance. As a result, the prior art focuses exclusively on ingesting substantial amounts of carbohydrate in a liquid form during endurance competition events. The prior art further teaches that supplementation with carbohydrate containing fluids is useful to prolong exercise and improve the performance of high intensity endurance exercise. Benefits to be obtained include maintenance of fluid balance and an increase in the availability of carbohydrate—the primary substrate for the muscular ATP production.

The present inventor has found, however, that it is not always logistically possible to consume large amounts of carbohydrate-containing beverages over extended periods of time. For example, heavy exercise in remote areas wherein any such beverages must first be carried for long distances prior to consumption renders such a prior art approach nonfeasible. Moreover, although considerable amounts of carbohydrates can be ingested, not all of the exogenous carbohydrates emptied from the stomach are oxidized during exercise.

In addition, gastric emptying rate decreases with increasing carbohydrate concentration and osmolality. Consequently highly concentrated carbohydrate solutions have been observed to increase the frequency of gastrointestinal distress in endurance athletes. Certain timing issues can further complicate the consumption of large amounts of carbohydrates. The efficiency of ingested glucose in enhancing physical performance is dependent on the time at which the beverage is ingested before exercise. It is known in the art that glucose containing beverages produce an increase in plasma glucose peaking approximately 45 minutes after ingestion. Such an increase in plasma glucose, however, results in an increase in plasma insulin and a subsequent drop in plasma glucose during the initial period of the activity, resulting in quick exhaustion. Thus, ingestion of large amounts of carbohydrates prior to embarking on a lengthy period of vigorous physical activity in the afore-mentioned remote area scenario can be deleterious rather than advantageous.

Creatine is sometimes used during exercise as a likely substance for the generation (in theory) of ATP through a reaction of phoshocreatine, due to the action of the enzyme creatine kinase (CK). However, administration of creatine can increase the propagation of methanal (formaldehyde). Clinical evaluation of urinalysis indicates insufficient excretion of methanal, leading to the indication of increased formaldehyde cell/tissue saturation as well as nephrotoxicity. Methanal is rarely encountered in living organisms, and when so, converts to formic acid. Formic acid, however, altogether prevents or significantly minimizes the generation of ATP because it induces a diminishing activity of the enzyme complexes within the Krebs cycle. It has been found by the inventor that creatine is disfavorable for the propagation of ATP from ADP and negates pyruvate dehydrogenase's activity.

DETAILED DESCRIPTION OF EXEMPLARY EMBODIMENTS

ATP is used in many key metabolic reactions and physiological functions. As exemplarily described herein, embodiments of the invention provide a composition having an active component which, when ingested by an animal (e.g., a human), can increase or maximize the biosynthesis potential of ATP within the animal and also increase the oxidation of several metabolic fuels such as carbohydrates and lipids within the animal. The active component of the composition is formulated to maintain a supply of ATP within the animal so that living cells within the animal can respond to circumstances such as stresses from exercise, starvation and pace the health of the cell; i.e., so that living cells can reproduce and grow. According to some embodiments, the active component of the composition includes ingredients such as niacin (or nicotinamide, or nictotinic acid), riboflavin, thiamine, pyruvate, ubiquinone, and lipoic acid (or thioctic acid). In one embodiment, the active component of the composition consists essentially of niacin (or nicotinamide, or nictotinic acid), riboflavin, thiamine, pyruvate, ubiquinone, and lipoic acid (or thioctic acid). In an embodiment, the active component of the composition does not contain any (or contains trace or insignificant amount of) ingredients such as creatine which inhibit or otherwise diminish the ability of the aforementioned active component of the composition to generate ATP within an animal (e.g., a human). In another embodiment, the active component of the composition consists only of niacin (or nicotinamide, or nictotinic acid), riboflavin, thiamine, pyruvate, ubiquinone, and lipoic acid (or thioctic acid). In another embodiment, an amount of creatine can be less than an amount of thiamine. A single dose of any composition described herein can be administered as often as every 20 minutes.

Although creatine has been given as an example of an ingredient that can diminish the generation of ATP, any ingredient that can diminish the generation of ATP can be either excluded, included in only trace amounts, or included in an amount less than one to all of other active ingredients of the composition.

Furthermore, although ingredients that can diminish the generation of ATP can be excluded from a composition, such ingredients can be present within an animal, included within a composition to an extent that does not exceed the animals need, ability to process, or the like. For example, creatine can be synthesized in an animal. The process can be controlled by a rate step limiting process. An amount of creatine can be included in a composition that does not override the limiting process and/or overwhelm the animal's ability to process resulting metabolites, such as formaldehyde and/or formic acid. If such conditions occur, the generation of ATP can be reduced.

Exemplary ranges for ingredients within the active component of the composition described herein are provided below in Table I. The amounts of each ingredient are given in milligrams (mg) per one dose of the composition.

TABLE I

| Ingredient | Amount per dose (mg) |
| --- | --- |
| Niacin (or nicotinamide or nictotinic acid) | 0.1 (or about 0.1) or greater |
| Riboflavin | 0.1 (or about 0.1) or greater |
| Thiamine | 0.1 (or about 0.1) or greater |
| Pyruvate | 0.1 (or about 0.1) or greater |
| Ubiquinone | 0.1 (or about 0.1) or greater |
| Lipoic acid (or thioctic acid) | 0.1 (or about 0.1) or greater |

In one embodiment, there is no upper limit to the amounts listed for any of the ingredients identified above in Table I. Furthermore, in an embodiment, no all of the ingredients of Table I need be used. For example, in an embodiment, the active ingredients can include niacin, riboflavin, pyruvate, and ubiquinone. That is, one or both of thiamine and lipoic acid need not be included.

According to another embodiment, exemplary ranges for ingredients within the active component of the composition described herein are provided below in Table II. The amounts of each ingredient are given in milligrams (mg) per one dose of the composition.

TABLE II

| Ingredient | Amount per dose (mg) |
| --- | --- |
| Niacin (or nicotinamide or nictotinic acid) | 1.2 (or about 1.2) to 2000 (or about 2000) |
| Riboflavin | 1.2 (or about 1.2) to 6000 (or about 6000) |
| Thiamine | 1.2 (or about 1.2) to 6000 (or about 6000) |
| Pyruvate | 1.2 (or about 1.2) to 6000 (or about 6000) |
| Ubiquinone | 1.2 (or about 1.2) to 2000 (or about 2000) |
| Lipoic acid (or thioctic acid) | 1.2 (or about 1.2) to 1000 (or about 1000) |

In one embodiment, pyruvate is the most abundant ingredient within the active component of the composition. That is, of the ingredients listed in Tables I and II, pyruvate is present in the highest weight percentage (wt. %) within the active component of the composition. Niacin (or nicotinamide or nictotinic acid) and riboflavin are present in the same (or about the same) wt. % within the active component of the composition, and the wt. % of each of these ingredients is less than the wt. % of pyruvate. The wt. % of ubiquinone present within the active component of the composition is less than the wt. % of niacin (or nicotinamide or nictotinic acid) or riboflavin. The wt. % of lipoic acid present within the active component of the composition is less than the wt. % of ubiquinone. The wt. % of thiamine present within the active component of the composition is less than the wt. % of lipoic acid. Exemplary amounts of ingredients within the active component of the composition, expressed as a percentage of the total weight of the active component of the composition (e.g., as described with respect to any of Tables I or II), are provided below in Table III.

TABLE III

| Ingredient | Amount per dose |
| --- | --- |
| Niacin (or nicotinamide or nictotinic acid) | 15.4% (or about 15.4%) |
| Riboflavin | 15.4% (or about 15.4%) |
| Thiamine | 7.9% (or about 7.9%) |
| Pyruvate | 37.3% (or about 37.3%) |
| Ubiquinone | 13.2% (or about 13.2%) |
| Lipoic acid (or thioctic acid) | 11.0% (or about 11.0%) |

The values given in Table III represent weight percentages of the ingredients where each of the ingredients may achieve optimal results. Deviation of the weight percentage of any of the ingredients by more than 60% may prevent the beneficial effects of the composition from being realized. For example, the values given in Table IV represent weight percentages of the ingredients where each of the ingredients may achieve acceptable results. However, the limits of the ranges of the examples of Table IV are not hard limits. That is, niacin, for example, could range from about 9.2% to about 25.7%.

TABLE IV

| Ingredient | Range per dose |
| --- | --- |
| Niacin (or nicotinamide or nictotinic acid) | 9.2%-25.7% |
| Riboflavin | 9.2%-25.7% |
| Thiamine | 4.7%-13.2% |
| Pyruvate | 22.4%-62.2% |
| Ubiquinone | 7.9%-22.0% |
| Lipoic acid (or thioctic acid) | 6.6%-18.3% |

In addition to the aforementioned active component, the composition may optionally include an excipient component. In one embodiment, the excipient component may include one or more of sodium ($Na^+$), calcium ($Ca^+$), potassium ($K^+$), magnesium ($Mg^+$), valine and aspartic acid. The sodium may be present in, for example, the form of sodium bicarbonate, or the like. The potassium may be present in, for example, the form of potassium bicarbonate, potassium citrate, or the like, or a combination thereof. The magnesium may be present in, for example, the fowl of magnesium citrate, or the like. The sodium may be present in, for example, the form of sodium bicarbonate, or the like. In one embodiment, one or more of these optional ingredients may be present, in one dose of the composition, in an amount of at least 0.1 (or about 0.1) mg. In another embodiment, one or more of these optional ingredients may be present, in one dose of the composition, in a range of amounts provided below in Table V.

TABLE V

| Ingredient | Amount per dose (mg) |
| --- | --- |
| $Na^+$ (optional) | 1.2 (or about 1.2) to 1000 (or about 1000) |
| $Ca^+$ (optional) | 1.2 (or about 1.2) to 2000 (or about 2000) |
| $K^+$ (optional) | 1.2 (or about 1.2) to 2000 (or about 2000) |
| $Mg^+$ (optional) | 1.2 (or about 1.2) to 2000 (or about 2000) |
| Valine (optional) | 1.0 (or about 1.0) to 1000 (or about 1000) |
| Aspartic acid (optional) | 1.0 (or about 1.0) to 1000 (or about 1000) |

Further, the excipient component may optionally include one or more of any of the twelve recognized cell salts. The twelve recognized cell salts include the calcium minerals (i.e., calcium fluoride, calcium phosphate and calcium sulphate), the potassium minerals (i.e., potassium chloride, potassium phosphate and potassium sulphate), the sodium minerals (i.e., sodium phosphate, sodium sulphate and sodium chloride) as well as ferrum phosphate (iron), magnesia phosphate (magnesium) and silicea (silica). The excipient component may also optionally include ingredients such as citric acid, sea salt, or the like or a combination thereof.

Having identified the ingredients of the active and the optional excipient components of the composition above, and exemplary amounts of each ingredient in the active component and the optional excipient component, and the weight percentage of each ingredient present in the active component, an explanation of the effect of the composition according to various embodiments of the present invention is set forth below.

When the composition is consumed by an animal (e.g., a human), the riboflavin delivers the fundamental hydrogen carrier flavin adenine dinucleotide (FAD), which is covalently bound to its dehydrogenase enzyme, and therefore may be defined as a prosthetic group. The biochemical reaction with FAD to the succinate dehydrogenase (SD) reaction reduces the FAD to $FADH_2$. SD is an integral component of the respiratory chain. When $FADH_2$ is oxidized by this process, a result of 1.5 ATP (adenosine triphosphate) moles is generated.

When the composition is consumed by an animal (e.g., a human), the niacin (or nicotinamide or nictotinic acid) generates nicotinamide adenine dinucleotide ($NAD^+$) which is a hydrogen carrier and is the coenzyme involved in several oxidation/reduction reactions. This coenzyme is recognized for its involvement with various oxidative/reduction reactions catalyzed by dehydrogenases. In the Krebs cycle event, malate dehydrogenase catalyzes the oxidation of malate to oxaloacetate. It is during this reaction that the $NAD^+$ is reduced to NADH (reduced nicotinamide dinucleotide). NADH is then oxidized by the respiratory chain, forming 2.5 moles of ATP.

$NAD^+$ is also recognized in its participation of metabolic reactions which transfer the potential free energy stored in lipids, carbohydrates and proteins to NADH, which is used to form ATP.

The electron transport involves the removal of electrons from NADH and/or $FADH_2$ transporting the electrons through the oxidative/reduction reactions involving cytochromes which then donate to oxygen. This then reduces to $H_2O$.

One of the most important mechanisms for synthesizing ATP relies on oxidative phosphorylation. This process is coupled with the oxidation of the reduced forms of riboflavin and niacin, $FADH_2$ and NADH, via the respiratory chain.

The mitochondrial respiratory chain encompasses a series of oxidative/reduction reactions within the recognized complexes 1, 2, 3 and 4. Ubiquinone and cytochrome link these reactions.

Ubiquinone, which encompasses Co enzyme Q10 and its family of ubiquinones, is involved in the electron transport and energy production (ATP) in the mitochondria. Thus, when the composition is consumed by an animal (e.g., a human), the ubiquinone accepts electrons from complex 1 and 2 which are activities vital for the generation of ATP molecules. Ubiquinone is reduced to ubiquinol which then shuttles from complex 1 to 3.

The synthesis of ATP via this respiratory chain is the result of the two coupled processes; oxidative phosphorylation and electron transport.

The electron transport "drives" proton pumps in the 1, 2, 3 and 4 complexes. As the charge separation occurs in this process the potential charge differential provides energy for ATP synthesis via the protons return to the matrix through the F0 proton channel which "drives" the F1 ATP synthetase.

Pyruvate is a key intermediate in both glycolytic and pyruvate dehydrogenase pathways. In the end product of glycolysis two molecules of pyruvate are fed into the Krebs cycle where they are oxidized to form $CO_2$. In this process, $NAD^+$ and FAD become reduced to NADH and $FADH_2$, thus carrying hydrogen into the respiratory chain. In this event, energy is conserved in ATP and the hydrogen is used to reduce oxygen into water. The pyruvate dehydrogenase reaction requires the cofactors derived from the niacin, thiamine, riboflavin and lipoic acid within the composition. An inadequate supply of these cofactors, either through inborn errors or insufficient utilization can cause a malfunctioning of the metabolic pathway at any number of the particular enzymatic reaction sites where the cofactor is involved. Pyruvate is often thought of as "the governor of glucose conservation". Pyruvate dehydrogenase determines if pyruvate is to enter the Krebs cycle for oxidation. When the composition is consumed by an animal (e.g., a human), pyruvate serves as a biological fuel by its conversion to acetyl coenzyme A which then enters the tricarboxylic acid (Krebs) and metabolized to generate ATP moles aerobically. In anaerobic events, energy can also be obtained from pyruvate via its conversion to lactate.

The coenzyme thiamine pyrophosphate (TPP) is derived from the thiamine in composition and participates in a number of group transfer reactions, the primary being pyruvate dehydrogenase and the oxidative decarboxylation of pyruvate to acetyl-CoA.

In the pyruvate oxidation phase, the proceeding acceptor of the aldehyde generated form TPP (thiamine pyrophosphate) is lipoic acid (thioctic acid). This transfer of the active aldehyde moiety from TPP involves oxidation of the aldehyde. This consequently generates an acyl group which in pyruvate dehydrogenase is transferred to coenzyme A.

The alkali metals potassium, magnesium, sodium and calcium (particularly the former potassium, magnesium and sodium) within the composition can be used in the composition as an adjunct to support the bicarbonate pool. Even though these elements are recognized for a wide variety of biological functions, their participatory role in regulating the pH can be beneficial in the composition, particularly during anaerobic phases of exercise. The "type" of ion or salt that these metals are attached to is for their stability. These are consequently known as alkaline salts.

Aspartic acid (e.g., L-aspartic acid) within the composition helps to remove ammonia from the liver via its cations interactions with ammonia has been recognized and is usually formed from one of intermediates of the Krebs cycle. This does not occur in adequate amounts when the Krebs cycle is compromised. Aspartic acid also promotes energy production via its metabolism in the Krebs cycle.

Citric acid is one of a series of compounds that acts as an intermediate in the Krebs cycle.

Homeopathic cell salts are prepared by serial dilutions. These inorganic constituents are the material basis of the organs and tissues in the body and help to maintain functional activity within the cells. In theory, any disturbance in the molecular supply (deficiency) of these salts can initiate a physiological imbalance. Administering these salts as part of the composition in small quantities can help bring about equilibrium within the system.

It will be apparent that the composition need not include the aforementioned coenzymes and cofactors such as NAD, NADH, FAD, and $FADH_2$ as these compounds are synthesized within the body when the composition is consumed by the animal. Likewise, the composition need not include compounds such as ATP, as this compound is synthesized within the body when the composition is consumed by the animal.

An exemplary composition formulated according to the embodiments described above is described below with respect to Table VI. Although a particular mass has been given, the actual mass can vary. For example, the mass of niacin can be about 35 mg.

TABLE VI

| Ingredient | Amount per dose (mg) |
| --- | --- |
| Niacin | 35 |
| Thiamine | 18 |
| Riboflavin | 35 |
| Lipoic acid | 25 |
| Pyruvate | 85 |
| CoQ10 | 30 |
| Aspartic acid | 25 |
| Sodium bicarbonate | 465 |
| Calcium carbonate | 160 |
| Magnesium bicarbonate | 105 |
| Potassium bicarbonate | 66 |
| Cell salts (6× homeopathic) | 2.5 |
| Citric acid | 13 |
| Sea salt | 7 |
| Potassium citrate | 3 |

According to some embodiments, any of the above-described compositions can be provided in the form of a tablet, a capsule, a powder, or the like or a combination thereof, in any suitable manner as is known in the art for oral administration. The powder may, for example, be mixed in a solvent such as liquid water.

Upon being consumed by an animal such as a human, a composition provided according to the embodiments exemplarily described above beneficially lowers triglycerides, increases potential of cellular energy (ATP), stabilizes pH, and increases efficiency of GTF (glucose tolerance factor). The composition can also increase the potential of ATP beyond the animal's natural ability to produce ATP because the presence and amounts of the ingredients within the composition synergistically increase the efficiency of the series of reactions within the Krebs cycle, thereby increasing the biosynthesis of ATP. The presence and amounts of the ingredients within the composition described herein also synergistically meet the optimal demands (maximum velocity) of the 7 primary enzymes found within mitochondria.

The inventor has discovered that, upon being consumed by an animal such as a human, the composition can also beneficially aid in weight loss because energy involved in oxidizing fat via hormone sensitive lipase is conserved as ATP.

The inventor has also discovered that, upon being consumed by an animal such as a human, the composition can contribute to cholesterol reduction lipoproteins (carriers of cholesterol) are reduced via the influence (activity) on HMG-CoA reductase. The antihyperlipidemic action of nicotinic acid is synergized by the interactions of the other ingredients in the composition.

The inventor has also discovered that, upon being consumed by an animal such as a human, the composition can temporarily improve vision because the visual sensory areas require adequate ATP production for optimal functioning.

The inventor has also discovered that, upon being consumed by an animal such as a human, the composition can reduce pain via lowering prostaglandin 2 (PG2).

The inventor has also discovered that, upon being consumed by an animal such as a human, the composition can alleviate respiratory distress. For example, respiratory distress can be alleviated due to the increase in ATP moles as well as diminishing the leukotrine responses. Leukotrines are fatty molecules which can be utilized as fuel moles for the propagation of ATP. Reduced leukotrines due to the increased generation of ATP can result in reduced bronchoconstriction, reduced inflammation, or the like alleviating respiratory distress.

The inventor has also discovered that, upon being consumed by an animal such as a human, the composition can increase cognizant acuity. For example, improved circulatory conditions as described herein, and/or the neuro-response from the increased generation of ATP can increase cognizant acuity.

The inventor has also discovered that, upon being consumed by an animal such as a human, the composition can reduce hypertension by increasing vascular efficiency.

The inventor has also discovered that, upon being consumed by an animal such as a human, the composition can address certain problems associated with erectile disfunction (e.g., influenced by neurogenic or arterial disorders) because the composition can heighten nerve response and increase vascular efficiency.

The inventor has also discovered that, upon being consumed by an animal such as a human, the composition increases the metabolism of glucose moles to yield maximum ATP moles in an anaerobic environment, thereby increasing the efficiency with which lactic acid is used by the body to produce energy.

The inventor has also discovered that, upon being consumed by an animal such as a human, lipoic acid in the composition is synergistically supported by the other ingredients to increase the potential for stimulating glucose uptake by muscle cells, in a manner similar to insulin, thereby positively influencing glucose control. Accordingly, hyperglycemia and hypoglycemia can be mitigated. Thus, this process is beneficial for addressing problems associated with diabetes.

While this invention has been particularly shown and described with reference to exemplary embodiments thereof, it will be understood by those skilled in the art that various changes in form and details may be made therein without departing from the spirit and scope of the embodiments described herein.

The invention claimed is:

1. A composition comprising:
    a plurality of active ingredients comprising pyruvate as the first active ingredient, niacin as the second active ingredient, riboflavin as the third active ingredient, ubiquinone as the fourth active ingredient, and lipoic acid as the fifth active ingredient;
    wherein the concentration by weight of the first active ingredient (pyruvate) in the composition is greater than the concentration by weight of each one of the other active ingredients; and
    wherein the composition comprises no creatine.

2. The composition of claim 1, wherein the plurality of active ingredients further comprises thiamine as a sixth active ingredient.

3. The composition of claim 2, wherein the plurality of active ingredients comprises:
    about 15.4% by weight niacin;
    about 15.4% by weight riboflavin;
    about 7.9% by weight thiamine;
    about 37.3% by weight pyruvate;
    about 13.2% by weight ubiquinone; and
    about 11.0% by weight lipoic acid.

4. The composition of claim 1, wherein the amount of pyruvate present in the composition is 85 mg.

5. The composition of claim 4, wherein the amount of niacin present in the composition is 35 mg.

6. The composition of claim 4, wherein the amount of riboflavin present in the composition is 35 mg.

7. The composition of claim 4, wherein the amount of lipoic acid present in the composition is 25 mg.

8. The composition of claim 4, wherein the plurality of active ingredients further comprises thiamine as a sixth active ingredient, and wherein the amount of thiamine present in the composition is 18 mg.

* * * * *

UNITED STATES PATENT AND TRADEMARK OFFICE
CERTIFICATE OF CORRECTION

| | |
|---|---|
| PATENT NO. | : 8,344,032 B2 |
| APPLICATION NO. | : 12/896162 |
| DATED | : January 1, 2013 |
| INVENTOR(S) | : Kevin Meehan |

It is certified that error appears in the above-identified patent and that said Letters Patent is hereby corrected as shown below:

In the Specifications:

Column 5, line 44, "the fowl of magnesium citrate" should be replaced with --the form of magnesium citrate--.

Signed and Sealed this
Twentieth Day of August, 2013

Teresa Stanek Rea
*Acting Director of the United States Patent and Trademark Office*